United States Patent [19]

Campbell et al.

[11] 4,036,210

[45] July 19, 1977

[54] DOUBLE LUMENED CATHETER

[76] Inventors: Roy L. Campbell, 3415 Canterberry St., Greensboro, N.C. 27408; Steven Loveland, 2904 Shadow Ridge Drive No. 7, Augusta, Ga. 30909

[21] Appl. No.: 585,067

[22] Filed: June 9, 1975

[51] Int. Cl.$^2$ .......................... A61B 10/00; A61M 25/00
[52] U.S. Cl. ............................................. 128/2 F; 128/240; 128/276; 128/208; 128/351
[58] Field of Search .............. 128/2 F, 240, 241, 276, 128/278, 348–351, 274, 208; 32/33

[56] References Cited

U.S. PATENT DOCUMENTS

| | | | |
|---|---|---|---|
| 2,812,765 | 11/1957 | Tofflemire | 128/276 |
| 2,826,197 | 3/1958 | Leonard | 128/240 X |
| 3,085,573 | 4/1963 | Meyer et al. | 128/240 |
| 3,136,316 | 6/1964 | Beall | 128/350 R |
| 3,208,145 | 9/1965 | Turner | 32/33 |
| 3,297,027 | 1/1967 | Rusch | 128/351 |
| 3,626,928 | 12/1971 | Barringer et al. | 128/241 X |
| 3,678,959 | 7/1972 | Liposky | 137/625.11 |
| 3,735,751 | 5/1973 | Katz | 128/240 X |
| 3,749,090 | 7/1973 | Stewart | 128/240 |
| 3,848,604 | 11/1974 | Sackner | 128/350 R |
| 3,945,385 | 3/1976 | Sackner | 128/350 R |

*Primary Examiner*—Dalton L. Truluck

[57] ABSTRACT

This invention comprises a novel aspiration-administration assembly which includes a fluid receptacle, a double lumened catheter, and a flow control means to simultaneously administer oxygen and perform aspiration functions.

4 Claims, 4 Drawing Figures

U.S. Patent  July 19, 1977  4,036,210
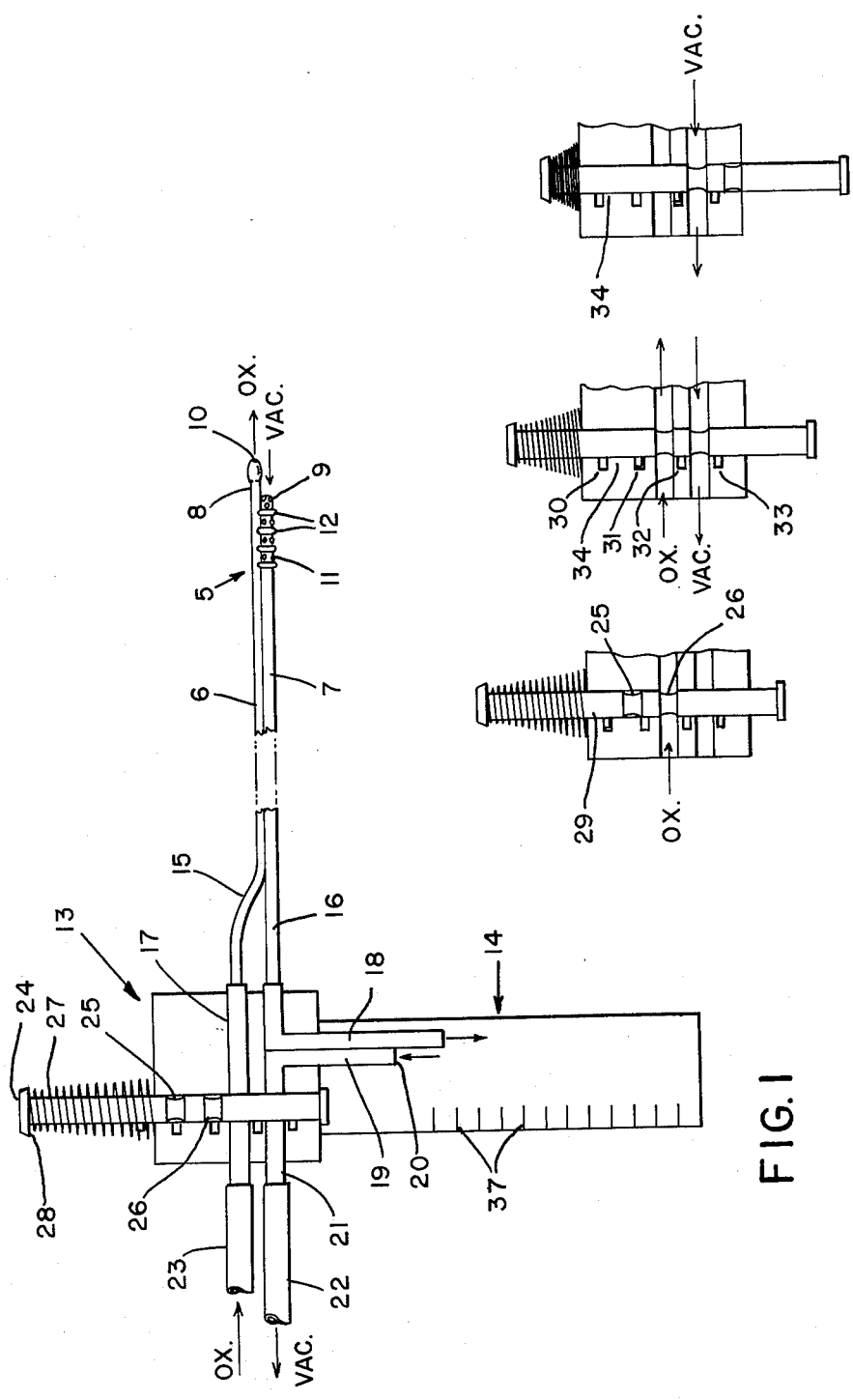

4,036,210

DOUBLE LUMENED CATHETER

BACKGROUND OF THE INVENTION

Medical science has long used catheters, which are tubelike structures, to remove fluids from various body cavities with the use of suction pumps or other similar equipment. Also, various catheters have been used as a means to convey fluids into various sections of the body. For example, intra-veinous feeding can be accomplished by catheterization.

In treating patients with lung disorders, it is frequently found that patients suffer from a lack of oxygen (hypoxia), a condition being directly attributable to the improper functioning of the lungs in the diseased condition. Also, it is quite common to have excess fluids in the lungs which additionally contribute to the detriment of the patient's health.

Therefore, multiple conditions exist in most lung ailments which require simultaneous treatment, and from this environment the present invention was developed.

OBJECTS OF THE INVENTION

It is one object of this invention to provide a double lumened catheter to simultaneously oxygenate and aspirate body cavities.

It is another object of this invention to provide a fluid receptacle that can be used as a sterile culture trap.

It is yet another object of this invention to provide a dual lumened catheter with a flow control means in which the operator can provide utilization of the oxygen catheter and the aspirator catheter independently, or simultaneously.

It is yet another object of this invention to provide a fluid receptacle with a graduated scale so that the operator can visually determine the amount of foreign matter removed from the patient.

It is yet another object of this invention to provide a flow control means which can quickly terminate either or both the oxygenation and aspiration action.

It is an additional object of this invention to provide a catheter tip which will prevent trachea erosion during its use.

IN THE DRAWINGS

FIG. 1 is a side view of the invention showing the catheter, control device and fluid receptacle;

FIG. 2 is a cross-sectional view of the control device adjusted to allow only the passage of oxygen;

FIG. 3 is a cross-sectional view of the control device adjusted to allow both passage of oxygen and withdrawal of fluid; and FIG. 4 is a cross-sectional view of the control device adjusted only to allow withdrawal of fluid from the patient.

For a more detailed description of the invention, referring to FIG. 1, the double lumened catheter 5 is shown with oxygenation lumen 6 positioned above aspiration lumen 7 in this embodiment. Oxygenation tip 8 is shown in advance of aspiration tip 9 so the individual fluid flow of each tip will not interfere with the other. Opening 10 is displayed at the terminal end of lumen 6 to flow outwardly while openings 11 are shown in tip 9 to receive fluids withdrawn from the body. Protuberances 12 are shown on tip 9 which prevent contact between the body tissues and openings 11 during fluid withdrawal.

Flow control device 13 is shown mounted on a fluid receptacle 14 and is attached to the oxygenation lumen 6 by tubing 15 and to aspiration lumen 7 by tubing 16. Passage 17 allows oxygen to flow through the control device from a conventional oxygen source. Tubing 16 is connected to inlet pipe 18 which allows passage of any foreign matter from the body to receptacle 14 by vacuum action. Intermediate outlet tube 19 maintains the vacuum action by virtue of its relatively high opening 20 above the collected fluid, allowing only gases to pass into the outlet tube 21 and to be returned through tubing 22 to a suitable vacuum source. Plunger 24 is designed with dual grooves 25 and 26 to allow simultaneous oxygenation and aspiration if desired. Spring 27 is constructed so it will not slide over shoulder 28 of plunger 24, and as the plunger is depressed spring 27 will urge plunger 24 upwardly and will frictionally maintain tab 29 in the desired recess.

Plunger tab 29 may form a bayonet type locking assembly with either recess 30, 31, 32, or 33 as shown in FIG. 3. Plunger 28 is rotated so tab 29 is positioned in channel 34 constructed to allow vertical movement of plunger tab 29 and by slight counterclockwise rotation of plunger 24, tab 29 is locked into the desired recess. Channel 34 is constructed to prevent loss of air or vacuum as plunger 24 is adjusted.

Fluid receptacle 14 is transparent or translucent to enable the technician to visually determine the amount of fluid withdrawn and is constructed of conventional sterilizable materials. Graduations 37 are placed on receptacle 14 so visual determination of the amount of fluid withdrawn can be determined at any time.

To use the double lumened catheter the operator would insert the catheter 5 into trachea of the patient and secure the tubing 15 and 16 to a convenient external portion of the patient's skin. The external terminal ends of tubes 15 and 16 are connected to the flow control means to which fluid receptacle 14 has been attached. The flow control means would then be attached by tube 23 to an oxygen source and tube 22 is similiarly attached to a vacuum source.

After the hook-up is completed, the catheter is ready for operation and either the oxygen source and/or vacuum source is activated depending on the requirements of the patient. If it is deemed advisable to initially oxygenate the patient, plunger is depressed and tab 29 is rotated into recess 31. Later, if it is necessary to both aspirate and oxygenate, plunger 24 is rotated clockwise so tab 29 is positioned in channel 34 before depressing plunger 24 enabling tab 29 to be rotated counterclockwise into recess 32. Likewise, if it is desired subsequently to only aspirate, then plunger 24 is rotated clockwise so that tab 29 will be positioned in channel 34 for downward movement and subsequent counterclockwise rotation into recess 33.

During the aspiration process, foreign matter is drawn into the openings 11 on catheter tip 9 and is conveyed through lumen 7 into receptacle 14. The amount of foreign matter removed through aspiration can be visually determined at any time by the graduations 37 which are on the receptacle's outer surface. Also, the receptacle can be quickly removed from the flow control means and can additionally serve as a specimen container during laboratory analysis of the foreign matter removed from the patient. Sterilized throwaway or reusable receptacles can be adapted and the convenience of the user so dictates.

Flow control means 13 is constructed to allow plunger 24 to control oxygenation and aspiration of the patient at a position proximate his bedside thereby facilitating adjustment and change of the catheter if either the oxygen source or vacuum source are located some distance away from the patients's room. As is shown in the drawings, the plunger can be moved either up or down when tab 29 is positioned in channel 34. However, if plunger 24 is released with tab 29 being so situated, the spring 27 forces plunger 24 upwardly and terminates both oxygenation and aspiration of the patient simultaneously, an added safety feature of this invention.

Tip 8 contains an opening 10 therein which allows the oxygen to flow outwardly for the patient's utilization. Tip 8 is advanced of tip 9, the aspiration tip, 1-2 centimeters to prevent mixing the fluids entering tip 9 through openings 11 and the oxygen flowing outwardly through tip 10.

During the aspiration process protuberances 12 prevent delicate skin tissues from being pulled into openings 11 as the vacuum action is maintained. Rather, protuberances 12 prevent contact between the tissues and the openings 11 and maximize the efficiency of tip 9.

We claim:

1. A multi-lumened catheter having at least two lumens, one of said lumens being an oxygenation lumen and the other being an aspiration lumen, each of said lumens having an opening therein, and a protuberance whereby the aspiration lumen is spaced by said protuberance from approximate tissue surfaces, said lumens having a common flow control means in communication therewith and having multiple flow positions for controlling independently or simultaneously the flow through said lumens, said control means having a plunger means, said plunger means having a locking tab member affixed thereto for locking said plunger means into the desired flow position for controlling the flow through said lumens.

2. A multi-lumen catheter as claimed in claim 1, wherein one lumen is connected to a fluid receptacle.

3. A multi-lumened catheter as described in claim 1, wherein said protuberance is circumferential disc member.

4. A multi-lumened catheter as described in claim 1, wherein said protuberance comprises a plurality of circumferential disc members.

* * * * *